United States Patent
Ross et al.

(10) Patent No.: US 8,453,546 B2
(45) Date of Patent: Jun. 4, 2013

(54) CAST-CUTTER AND METHOD

(75) Inventors: David J. Ross, Stirling (GB); George Miller, Midlothian (GB)

(73) Assignee: Ross Wark Medical Limited, Cambusbarron, Stirling (GB)

( * ) Notice: Subject to any disclaimer, the term of this patent is extended or adjusted under 35 U.S.C. 154(b) by 838 days.

(21) Appl. No.: 10/599,139

(22) PCT Filed: Mar. 23, 2005

(86) PCT No.: PCT/GB2005/001158
§ 371 (c)(1),
(2), (4) Date: Dec. 7, 2006

(87) PCT Pub. No.: WO2005/092267
PCT Pub. Date: Oct. 6, 2005

(65) Prior Publication Data
US 2007/0227319 A1    Oct. 4, 2007

(30) Foreign Application Priority Data
Mar. 23, 2004  (GB) .................... 0406443.2

(51) Int. Cl.
*B26B 13/00*    (2006.01)
*B26B 13/06*    (2006.01)
*B26B 15/00*    (2006.01)

(52) U.S. Cl.
USPC ............. 83/13; 83/56; 83/102.1; 30/131; 30/228; 30/233; 30/249; 30/253; 30/277.4; 30/289

(58) Field of Classification Search
USPC .......... 30/194, 254, 131, 132, 179, 180, 30/186–188, 227, 228, 233, 244–247, 249, 30/253, 272.1, 277.4, 286, 289; 83/23, 27, 83/34–36, 56, 102.1, 614
See application file for complete search history.

(56) References Cited

U.S. PATENT DOCUMENTS

| | | | | |
|---|---|---|---|---|
| 840,468 | A | * | 1/1907 | Bennett ..................... 30/233 |
| 1,321,918 | A | * | 11/1919 | Herman ..................... 30/228 |
| 2,045,050 | A | * | 6/1936 | O'Banion .................. 30/142 |
| 2,264,840 | A | * | 12/1941 | Isaac ........................ 30/254 |
| RE30,718 | E | | 8/1981 | Etchell |
| 5,901,447 | A | | 5/1999 | Dunning |
| 5,993,303 | A | | 11/1999 | Fladgard et al. |
| 6,145,203 | A | * | 11/2000 | Appleman ................. 30/233 |
| 2001/0037712 | A1 | * | 11/2001 | Furuhata et al. .......... 83/694 |
| 2005/0028381 | A1 | * | 2/2005 | Foshag ..................... 30/233 |

FOREIGN PATENT DOCUMENTS

| DE | 20219556 | | 4/2003 |
|---|---|---|---|
| EP | 0 156 395 | * | 10/1985 |
| EP | 0950474 | | 10/1999 |
| EP | 1411534 | | 4/2004 |
| EP | 1506705 | | 2/2005 |
| GB | 469230 | | 12/1936 |

* cited by examiner

*Primary Examiner* — Clark F. Dexter
(74) *Attorney, Agent, or Firm* — Gifford, Krass, Sprinkle, Anderson & Citkowski, P.C.

(57) ABSTRACT

A cast-cutter (10) for removing a cast from a patient comprises a body (12) and a cutting assembly (18) secured thereto, wherein the cutting assembly (18) includes first and second relatively moveable cutting members (40, 44). Each cutting member (40, 44) defines a cutting edge (46, 48) which when in use cooperate to cut by a shearing action. Each cutting member (40, 44) also defines an inner face (60) and are adapted to maintain the inner faces (60) in non-engaging relationship to provide clearance therebetween in order to prevent material binding between the member (40, 44) during a cutting operation.

11 Claims, 18 Drawing Sheets

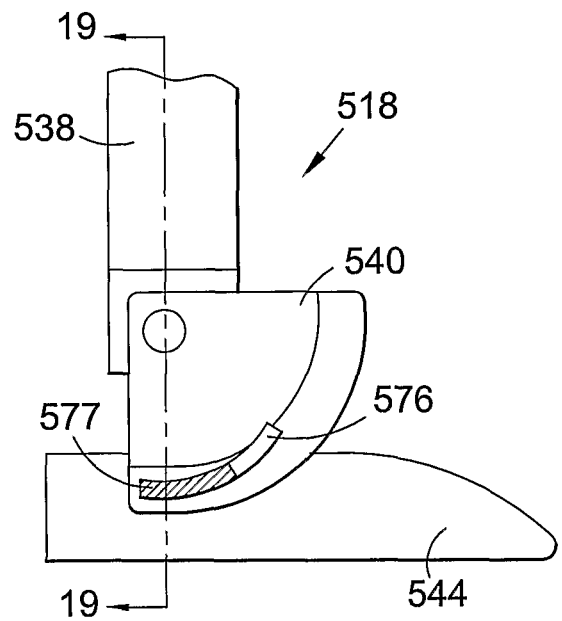
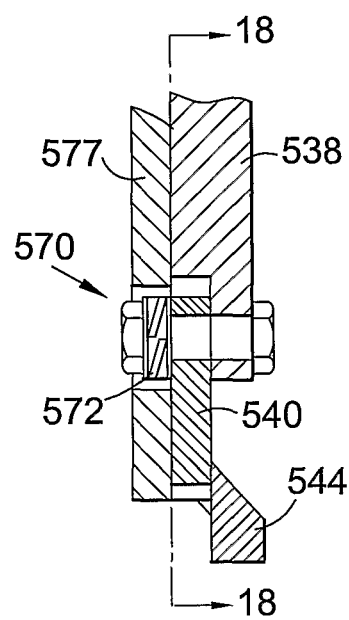
Fig. 18     Fig. 19
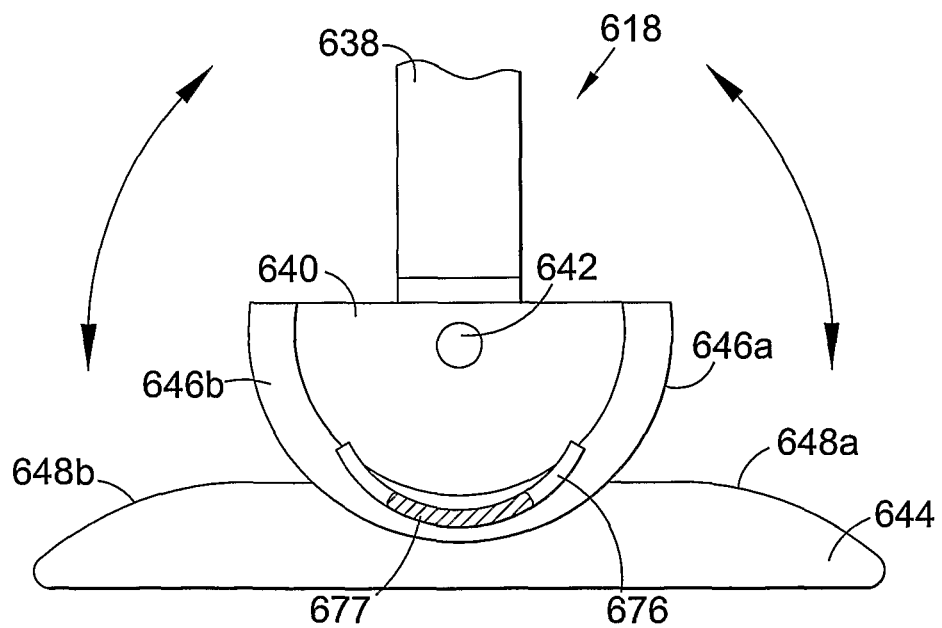
Fig. 20

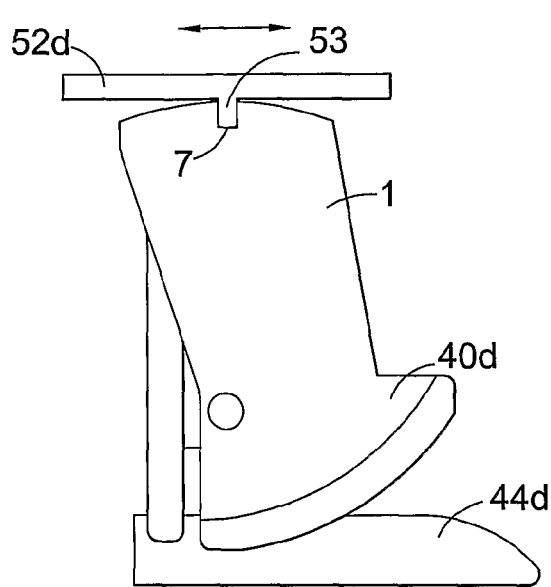
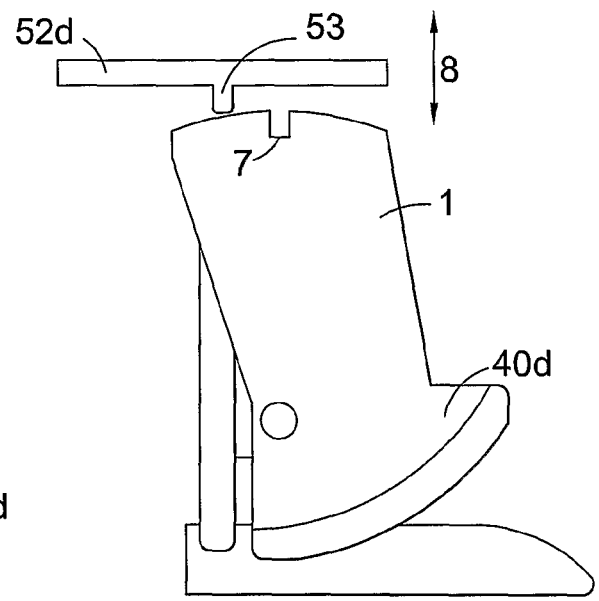
Fig. 31   Fig. 32
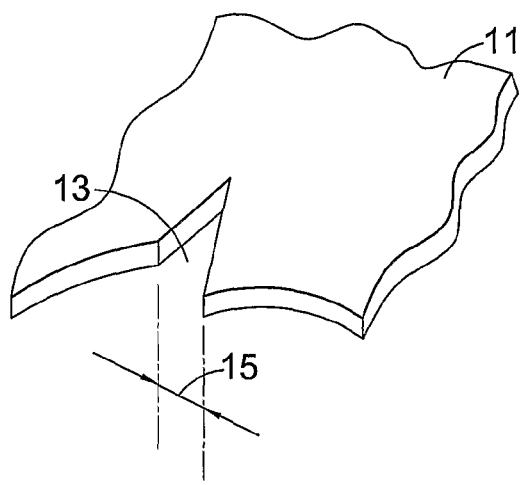
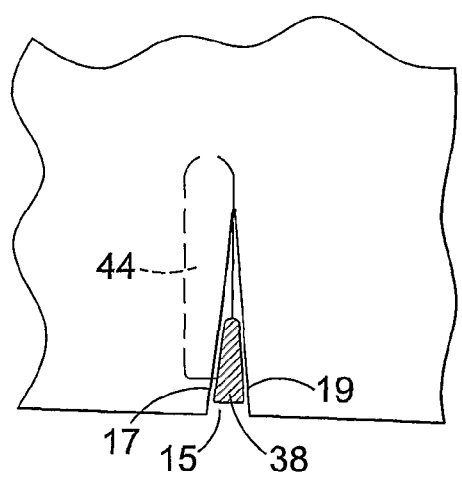
Fig. 33   Fig. 34

CAST-CUTTER AND METHOD

FIELD OF THE INVENTION

The present invention relates to a cutter, and in particular, but not exclusively, to a cutter for use in removing a cast used to immobilize an injured body part from a limb or otherwise of a patient.

BACKGROUND TO THE INVENTION

Typical "plaster" casts for use in immobilising limbs or other parts of the body are composed of a padded fibre layer surrounded by a plaster or fibreglass tape layer. Conventional cast-cutters remove such casts by cutting through the plaster or fibreglass layer, with the padded layer subsequently being cut using scissors, or other like instruments. This is normally repeated at opposing sides of the cast to enable the cast to be removed in two sections.

Conventional cast-cutters typically comprise an oscillating blade or disc which abrades or saws the plaster or fibreglass. As a result, large quantities of dust may be produced and dispersed within the air. In order to minimise the release of dust particles, a dust extraction device may be required, which may be cumbersome and adds additional expense to the cutting device.

Furthermore, conventional cutters are generally noisy in operation due to the action of the blade cutting the cast material, in combination with a high-speed motor, and also due to the presence of the extraction device. The noise produced can be distressing, particularly to young patients, which may result in patients becoming agitated, making removal of the cast without causing injury more difficult. Additionally, the noise produced by conventional cast-cutters can present significant health and safety issues in that an operator should not be exposed to elevated noise levels for prolonged periods of times. Accordingly, in many jurisdictions, the length of time which an operator may use a conventional cast-cutter is restricted.

Additionally, in use, the blades of conventional cutters may become heated due to friction between the blade and the cast, which introduces the risk of burning the skin of the patient.

Further, conventional cast cutters which utilise a sawing action to remove a cast are known to produce significant levels of vibration which can be transmitted to the user, and indeed the patient, which is preferably to be avoided.

Due to the above problems, cast cutters which involve cutting the cast by a sawing action, even when operated by a skilled operator, may result in distress and injury to the patient, and give rise to health and safety considerations for the operator.

A cast cutter which seeks to solve the above noted problems is disclosed in Applicant's patent application publication number WO 2004/026207, the disclosure of which is incorporated herein by reference.

It is among objects of embodiments of the present invention to obviate or at least mitigate the aforementioned and other problems with the prior art.

SUMMARY OF THE INVENTION

According to a first aspect of the present invention, there is provided a cast-cutter for use in removing a cast from a patient, said cast-cutter comprising:
a body; and
a cutting assembly mountable on the body and comprising first and second relatively moveable cutting members each defining a cutting edge and a inner face, wherein the first and second cutting members are adapted to permit cooperation between the respective cutting edges to cut by a shearing action while maintaining the inner faces in non-engaging relationship to provide clearance therebetween.

Advantageously, in use, the cast-cutter of the present invention may be manipulated to position a cast material to be removed from a patient between the first and second cutting members, and subsequently activated to cause relative movement of the first and second cutting members to cause the cast material to be cut by cooperation of the cutting edges. The clearance provided between the respective inner faces advantageously prevents the cast material from binding between the cuffing members during a cutting operation, which may otherwise cause unnecessary wear and ultimately damage the cutting members and possibly the cutting assembly, and may also cause the cutting members to be splayed apart while increasing the frictional load on the cutting assembly.

Preferably, the first and second cutting members of the cutting assembly are arranged such that during a cutting operation the cutting edges are aligned with a projected cutting plane, such that the cutting edges are adapted to engage and cooperate to produce a shearing strain in the cast material in order to cut the cast material through the projected cutting plane. Advantageously, in some embodiments of the present invention the entire length of the cutting edges, or a substantial portion thereof, may be aligned with a projected cutting plane at the same time. In alternative embodiments discrete portions of the cutting edges may be aligned with a projected cutting plane at any one time. Thus, as the first and second cutting members are moved relative to each other to effect cutting, the discrete point at which the cutting edges are aligned with the projected cutting plane will move along the length of the cutting members, in the direction of cut.

Preferably, an inner face of at least one of the cutting members is inclined outwardly from a projected cutting plane in order to provide clearance between the inner faces when the cutting assembly is operated. More preferably, the inner face of both cutting members are outwardly inclined from the projected cutting plane in order to provide clearance between said faces when the cutting assembly is operated.

Advantageously, the shearing action of the cast-cutter allows the cutting assembly to cut through the entire thickness of the cast, through both rigid and padded fibre or bandage layers, for example, eliminating the requirement for scissors or the like to cut through soft material once the rigid material has been cut using conventional methods.

However, if required, the cutting assembly may cut through the rigid layer only, with the padded fibre layer or bandage layers being subsequently cut using conventional scissors or the like.

Cutting a cast material by a shearing action substantially reduces the noise, dust and other problems normally associated with rotating or oscillating blades, which thus reduces patient discomfort and anxiety, and also increases user safety.

Preferably, the cutting assembly of the cast-cutter is adapted to cut various types of casts, including plaster casts and synthetic, glass fibre casts which may comprise glass fibre tape or other similar rigid casting material.

The cutting assembly may be adapted to cut a cast in two directions.

Preferably, one of the first and second cutting members is fixed relative to the body, and the other cutting member is moveable, such that in order to effect cutting of a section of a cast the moveable member is moved towards the stationary member when the cast is positioned therebetween.

Preferably, one of the cutting members is pivotally mounted relative to the other cutting member. In one embodiment, one member may include a lug which is accommodated in a suitable recess or land area on the other member.

Alternatively, one of the cutting members may be mounted to be reciprocally moveable along a linear path relative to the other cutting member.

Alternatively further, one of the first and second cutting members may be rotatably mounted relative to the other cutting member and may be suitably formed and arranged to shear a cast material upon rotation.

Alternatively further, the first and second cutting members may be moveable such that cutting is achieved by movement of the first and second members towards each other.

Preferably, the cutting assembly comprises a support member adapted to support the first and second cutting members. Preferably, the support member is adapted to fixedly support one of the first and second cutting members and to moveably support the other cutting member so that relative movement between the first and second cutting members may be achieved.

Advantageously, one cutting member may be integrally formed with the support member, or alternatively may be separately formed and rigidly secured thereto, for example by welding, bolting, riveting, clamping or the like.

In a preferred embodiment of the present invention, the other of the first and second cutting members is moveably supported on the support member by being pivotally coupled thereto. Advantageously, the pivotally mounted cutting member may be coupled to the support member by means of a pivot pin arrangement. The pivot pin arrangement may be provided by, for example, a bolt, cantilever pin, press-fit pin, or the like.

In an alternative embodiment of the present invention, both the first and second cutting members may be non-rigidly connected to the support member of the cutting assembly.

Preferably, the cutting assembly is adapted to be releasably mountable on the body of the cast-cutter. This arrangement advantageously permits the cutting assembly to be readily removed from the cast-cutter for inspection, repair, re-sharpening or to be entirely replaced, for example. The ability to readily replace the entire cutting assembly also offers significant advantages in that the possibility of transmitting infection from patient to patient may be minimised.

The cutting assembly may be adapted to be secured to the body in alternate directions such that the cast-cutter may be used to cut a cast in at least two directions.

Preferably, the support member of the cutting assembly is adapted to be mountable on the body of the cast cutter in order to secure the cutting assembly thereto. The support member may be adapted to be mountable on the body by way of a suitable bracket or flange arrangement or the like, and may be secured to the body by use of, for example, bolts, screws, a quick-release mechanism or the like. Alternatively, the support member may be mountable on the body by way of a suitable threaded connection, for example.

Preferably, the cutting assembly further comprises biasing means for biasing at least the cutting edges of the first and second cutting members laterally together. Advantageously, the biasing means provides a positive pressure between the first and second cutting members of the cutting assembly to assist in preventing lateral separation or splaying of the cutting members and to ensure an efficient cutting action is achieved and maintained.

The biasing means may comprise spring biasing means, such as a sprung washer or a disc type spring or the like. Alternatively, or additionally, the biasing means may be provided by one or both of the first and second cutting members, for example by providing one or both members with a longitudinal curvature or profile. The curvature or profile, in use, may be adapted to cause an interference engagement between the cutting edges of the first and second cutting members causing one or both members to elastically deform, wherein the force of elastic recovery within one or both members acts to bias the cutting edges into contact engagement with each other.

Advantageously, the respective cutting edges of the first and second members may be provided as or on separate inserts or components which are secured to the first and second members respectively. The inserts may be releasably secured to the respective first and second portions such that if a cutting edge becomes damaged or inefficient, it may be readily replaced without the need to replace the entire member upon which the cutting edge is located. Additionally, the provision of cutting edges on separate inserts allows the first and second members of the cutting assembly to be manufactured from a first material which does not have to exhibit the required mechanical properties to directly cut a cast material, which would generally be more expensive. The inserts may be manufactured from any suitable material such as polymeric, ceramic or metal or the like.

Preferably, in use, one of the first and second cutting members is adapted to be positioned underneath a cast, between the cast material and the skin of a patient. Preferably, the cutting member to be positioned between the cast material and the skin of a patient may advantageously be utilised as a protecting member to protect the patient from injury while the cast-cutter is in use.

Preferably, the cutting assembly is adapted to be coupled to a drive means via a drive mechanism, wherein the drive mechanism transmits motion from the drive means to the cutting assembly for causing relative movement between the cutting members to effect cutting.

In a preferred embodiment of the present invention, the drive mechanism is adapted to reciprocate. In this preferred embodiment the drive mechanism may comprise a reciprocating drive pin coupled to the drive means by a suitable transmission arrangement, and also coupled to one of the cutting members.

In an alternative arrangement, the drive mechanism may be adapted to rotate or oscillate or the like.

In a preferred embodiment of the present invention, the drive mechanism is adapted to terminate the connection between the drive means and the cutting assembly upon reaching a predefined force exerted by the cutting assembly, and specifically between the cutting members. This arrangement advantageously minimises the possibility of causing damage to the cutting assembly by attempting to cut a material which may be beyond the safe capability of the particular cutting assembly. In one embodiment of the present invention the drive mechanism may comprises a slip pin or shear pin coupling arrangement adapted to be activated or sheared when the predefined force is reached.

Preferably, the cutting assembly is operated by electric drive means. Preferably, the electric drive means comprises an electric motor. Advantageously, control circuitry may be provided and adapted to permit the required control of the electric motor to be achieved. The control circuitry may incorporate safety features such as thermal and current tripping circuits. For example a self-resetting current tripping circuit may be provided which is adapted to prevent or cease operation of the cast-cutter upon reaching a predetermined current load.

Preferably, the electric motor comprises braking means adapted to prevent movement of the cutting means when the cast-cutter is deactivated. In a preferred embodiment of the present invention, the braking means is provided by permitting the electric motor to be short-circuited to generate a transitory back e.m.f. to rapidly stop rotation of the motor. Advantageously, the cast-cutter may comprise one or more electrical resistors through which the electric motor may be short-circuited in order to accommodate a brief surge in the current when the cast-cutter is deactivated, and to thus protect the components and electrical connections of any control circuitry.

Alternatively, the cutting assembly may be operated by hydraulic drive means. Alternatively further, the cutting assembly may be operated by pneumatic drive means.

Advantageously, the cast cutter may be powered by an electrical power supply, such as a mains supply either alone or in combination with a transformer and/or a rectifier, or alternatively, or indeed additionally, by a local power supply such as a battery pack.

Advantageously, the cast-cutter may include visual signal means which are activated when power is supplied thereto. Such visual signal means may comprise one or more LEDs or the like.

Conveniently, the cast-cutter may be activated by depressing or otherwise closing a normally open main switch, and deactivated by releasing said switch.

Preferably, the cast-cutter comprises at least one safety switch which must be depressed or released before the cast-cutter can be operated by the main switch. This prevents the cast-cutter from being inadvertently activated by accidentally depressing the main switch. Advantageously, visual signal means may be provided and activated when the at least one safety switch is operated.

In a preferred embodiment of the present invention, the cast-cutter comprises two safety switches, wherein at least one of the two safety switches must be depressed or otherwise activated before the cast-cutter may be operated by the main switch. Advantageously, one of the two safety switches is positioned on the cast-cutter to permit ease of use by a right-handed operator, and the other of the two safety switches is positioned to permit ease of use by a left-handed operator.

Preferably, the cast-cutter further comprises a safety guard disposed around the cutting assembly to prevent accidental injury by trapping a finger, for example, while the cutter is in use. The guard may be fixed in place or alternatively may be retractable to allow access to the cutting assembly for cleaning or maintenance, for example. Where the safety guard is retractable, the guard may include a safety switch such that the cast-cutter may only be operated when the safety guard is positioned correctly in place.

In a preferred embodiment of the present invention, the cast-cutter comprises a safety guard having a fixed portion and a retractable portion moveably mounted on the fixed portion. In this embodiment, the retractable portion is adapted to be retracted to permit access to the cutting assembly, for example to engage a cast material during a cast removal operation. Preferably, the retractable portion is pivotally mounted on the fixed portion.

Preferably, the safety guard is transparent such that the cutting assembly may be safely viewed by a user to ensure correct operation and that a correct line of cut is being achieved.

Advantageously, the various components of the cast-cutter may be coated with a material to prolong service life or to allow ease of cleaning or the like. For example, a Teflon® coating may be utilised.

Advantageously also, various portions of the cast-cutter may be hardened to ensure longevity. For example, the cutting edges of the cutting members may be hardened, for example using mechanical or chemical hardening techniques.

According to a second aspect of the present invention, there is provided a method of removing a cast from a patient, said method comprising the steps of:
providing a cast cutter according the first aspect;
manipulating the cast-cutter to position a cast material to be removed from a patient between the first and second cutting members; and
activating the cast-cutter to cause relative movement of the first and second cutting members to cause the cast material to be cut by cooperation of the cutting edges.

According to a third aspect of the present invention, there is provided a switching arrangement for use with a hand operated device having a central plane, said arrangement comprising:
a primary operating switch mounted substantially on said plane;
a first secondary operating switch mounted to be offset from said plane in a first direction; and
a second secondary operating switch mounted to be offset from said plane in an opposite second direction;
wherein the primary operating switch may be activated to operate the hand operated device when at least one of the first and second operating switches is activated.

Accordingly, the switching arrangement advantageously permits the hand-operated device to readily accommodate both left and right hand operators.

Preferably, in normal use, the primary switch is adapted to be operated by an operator's trigger finger. Preferably also, in normal use, one of the first and second secondary switches is adapted to be operated by the operator's thumb of one hand, and the other secondary switch is adapted to be operated by the operator's thumb of the other hand.

The switching arrangement advantageously may be adapted for use with a cast-cutter for removing a cast from a patient. The switching arrangement may also be adapted for use with hand held power tool such as a drill, jigsaw, sander, router or the like.

BRIEF DESCRIPTION OF THE DRAWINGS

These and other aspects of the present invention will now be described, by way of example only, with reference to the accompanying drawings, in which:

FIGS. 8 to 26 show various embodiments of cutting assemblies which operate in a pivoting motion in accordance with the present invention;

FIGS. 27 to 32 show various embodiments of drive mechanisms in accordance with the present invention;

FIG. 33 is a perspective view of a cast material with a cut area;

FIG. 34 is an elevation view of a cast material with a portion of a cast-cutter according to an embodiment of the present invention shown when in use;

DETAILED DESCRIPTION OF THE DRAWINGS

Figure 1:
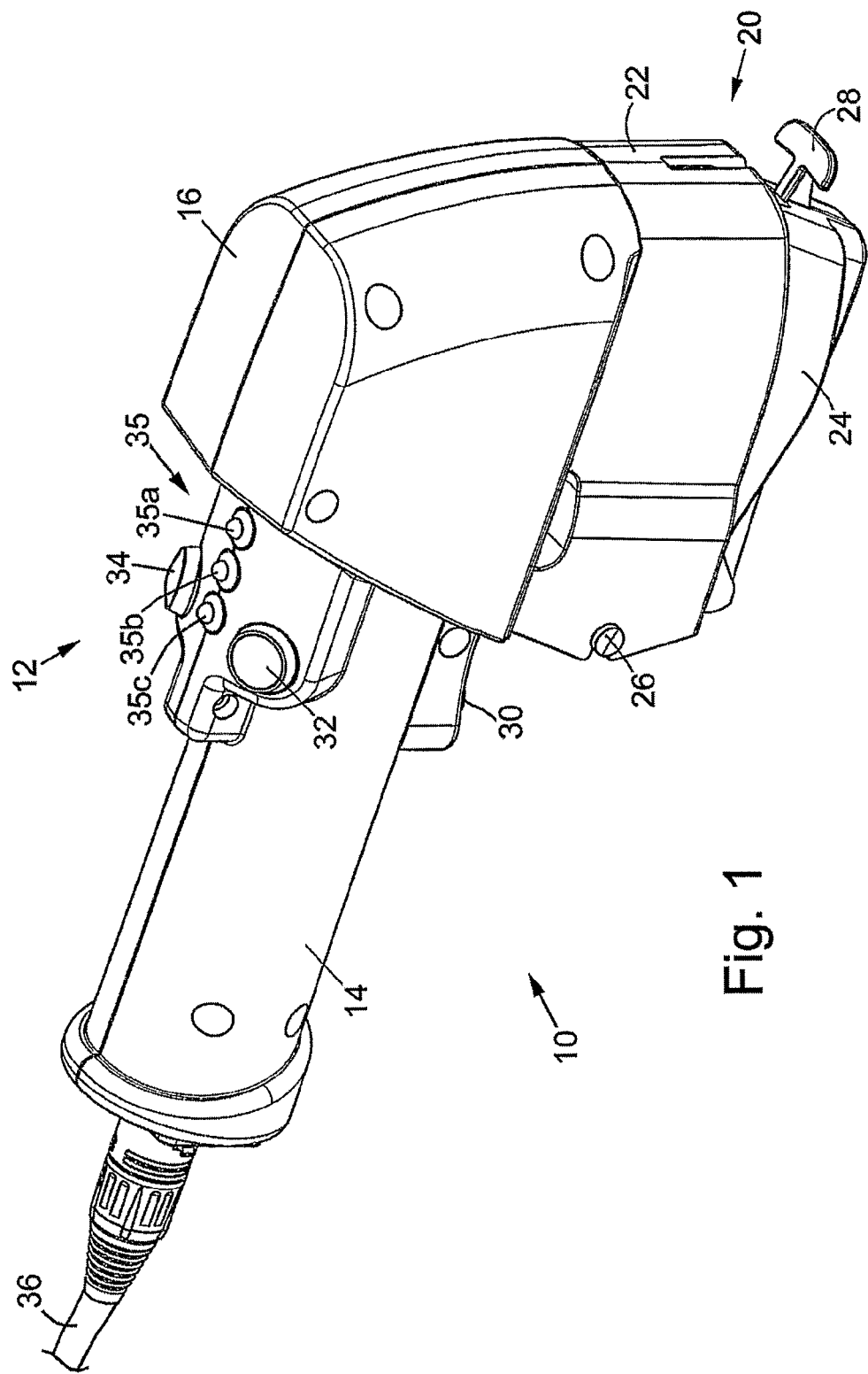
FIG. 1 is a perspective view of a cast-cutter in accordance with an embodiment of the present invention.
Figure 2:
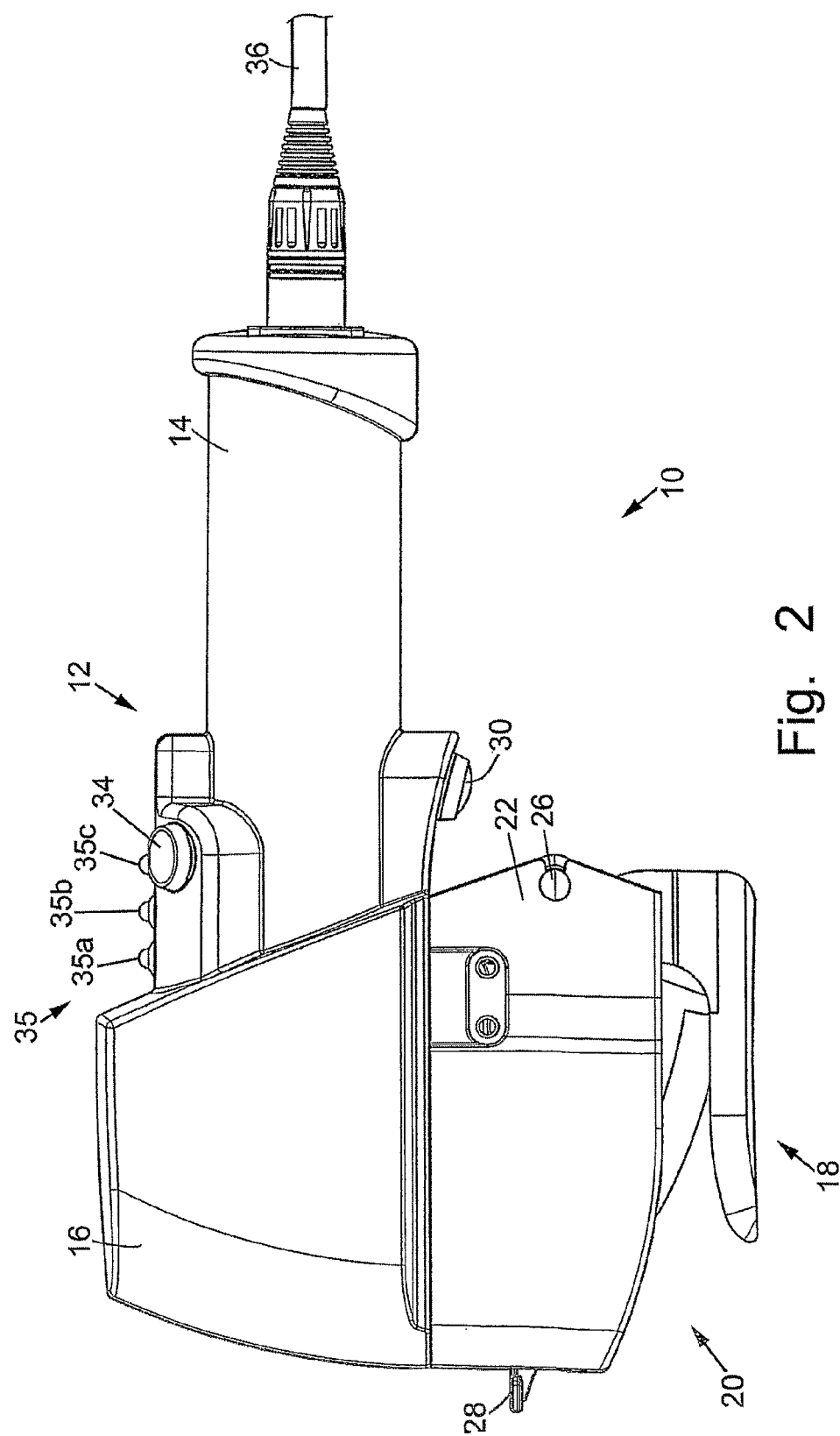
FIG. 2 is a side view of the cast-cutter of FIG. 1.

Reference is first made to FIGS. 1 and 2 of the drawings in which there is shown alternative views of a cast-cutter 10 in accordance with an embodiment of the present invention. The cast-cutter 10 comprises a body 12 incorporating a handle portion 14 and a head portion 16, upon which head portion is mounted a cutting assembly 18 (FIG. 2). A safety guard 20 is secured to the head portion 16 to surround the cutting assembly 18. The safety guard 20 comprises a fixed portion 22 and a retractable portion 24 (FIG. 1) pivotally mounted on the fixed portion 22 via pivot 26. The retractable portion 24 incorporates a lever 28 so that a user may retract portion 24, for example to align the cutting assembly 18 with a cast to be removed from a patient. The retractable portion 24 is shown in an extended position in FIG. 1, and in a retracted position in FIG. 2.

The cast-cutter 10 further comprises a main switch 30 and two safety switches 32, 34, all located on the handle 14, said switches 30, 32, 34 for activating the cutting assembly 18. Operation of the cutting assembly 18 is achieved by simultaneously activating the main switch 30 and one of the two safety switches 32, 34. The switching arrangement is such that a right handed operator may grip the handle 14 with their right hand and operate the main switch 30 with their trigger finger and safety switch 34 with their thumb, thus providing a comfortable operating position. Similarly, a left handed operator may grip the handle 14 with their left hand while operating the main switch 30 with their trigger finger and safety switch 32 with their thumb, again providing a comfortable operating position.

In the embodiment shown, the cast-cutter 10 is operated by an electric D.C. motor (not shown) positioned within the body 12 and provided with electrical energy via electrical cable 36. As shown, the handle 14 is aligned with the intended direction of cut which provides a user with improved control when using the cast-cutter 10.

A visual light display 35 is provided which incorporates three LEDs 35a, 35b, 35c which are adapted to visually convey the operational status of the cast-cutter. In the embodiment shown, LED 35a indicates if power is being supplied to the cast-cutter 10, LED 35b indicates if one of the safety switched 32, 34 is depressed, and LED 35c indicates if the main switch 30 has been depressed. Thus, when all LEDs are illuminated the cast-cutter is in operation.

Figure 3:
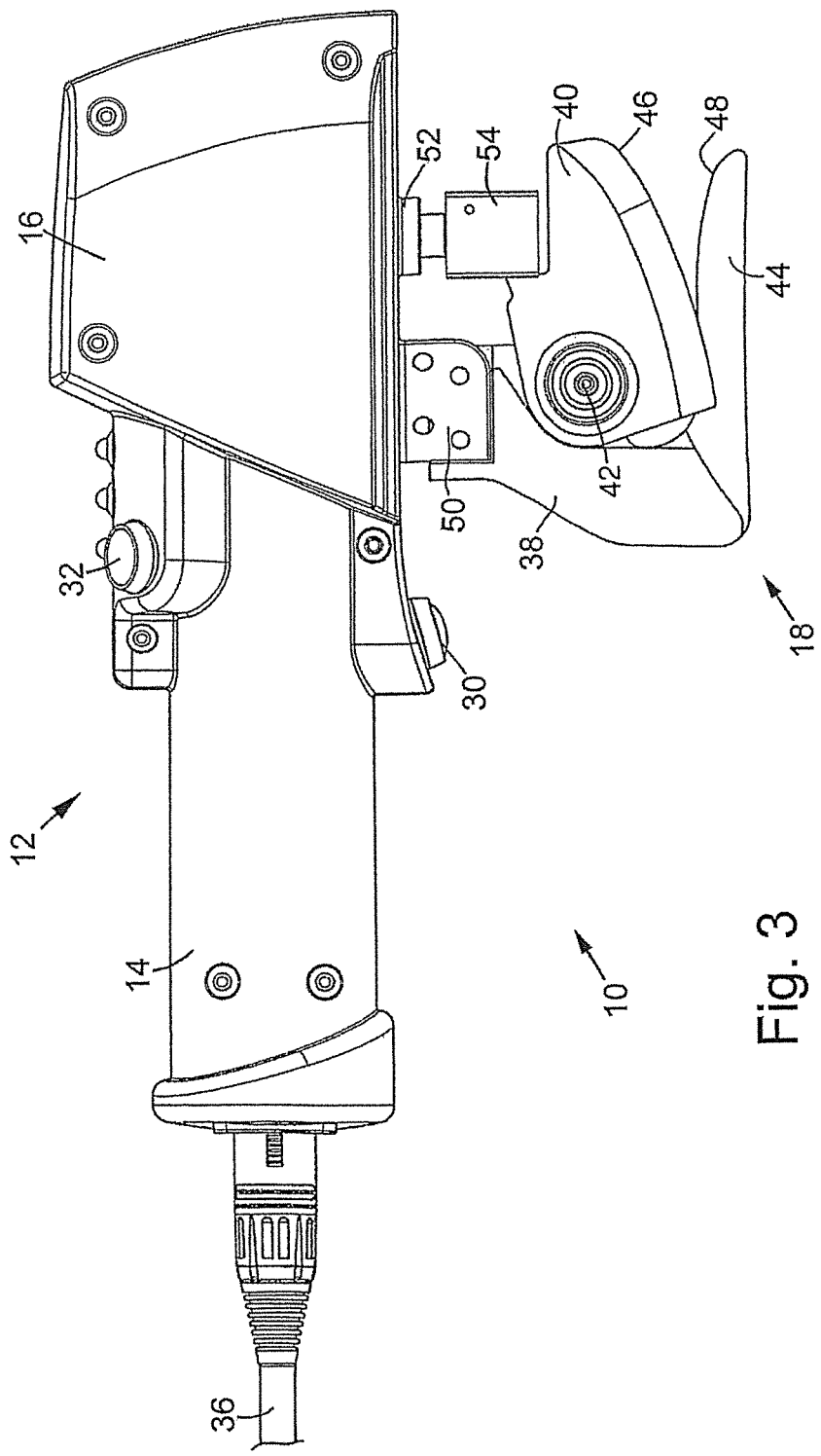
FIG. 3 is an alternative side view of the cast-cutter of FIG. 1 with a safety guard removed.

Reference is now made to FIG. 3 in which the cast-cutter 10 of FIGS. 1 and 2 is shown with the safety guard 20 removed to expose the cutting assembly 18. The cutting assembly 18 comprises a support member 38, a pivoting cutting member 40 pivotally mounted on the support member 38 via pivot 42, and a stationary cutting member 44 rigidly secured to the support member 38. The cutting members 40, 44 incorporate respective cutting edges 46, 48 which in use cooperate to cut a cast material by a shearing action.

The support member 38 is releasably mounted on the body 12 of the cast-cutter 10 via a bracket and bolting arrangement 50 (bolts not shown). Accordingly, the entire cutting assembly 18 may be removed from the cast cutter 10 for inspection, repair, resharpening or replacement or the like.

The pivoting cutting member 40 is releasably coupled to a reciprocating drive rod 52 via fixing 54, such that the reciprocating rod 52 may cause the pivoting member 40 to move relative to the fixed member 44 to effect cutting. The fixing 54 is advantageously a removeable component which assists to transmit reciprocal motion of the rod 52 to pivoting motion of the member 40. The reciprocating rod 52 is coupled to the electric motor (not shown) via a suitable transmission arrangement (also not shown).

In use, the retractable portion 24 (FIG. 1) of the guard 20 may be retracted to position the edge of a cast to be removed between the cutting edges 46, 48 of the cutting members 40, 44. The cast-cutter 10 may then be activated by the switching arrangement 30, 32, 34 to move the pivoting cutting member 40 relative to the stationary cutting member to thus effect cutting of the cast material. The cast-cutter 10 may then be moved along the length of the cast to remove said cast from the patient, wherein the stationary cutting member slides between the cast and the patient's skin, thus acting to protect the patient from injury.

Figure 4:
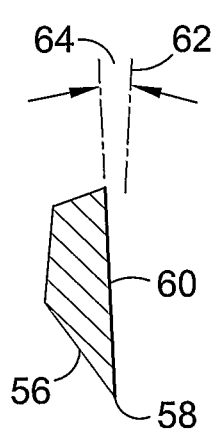
FIGS. 4 to 7 show cross-sectional views of cutting members for use in the cast-cutter of FIG. 1.
Figure 5:
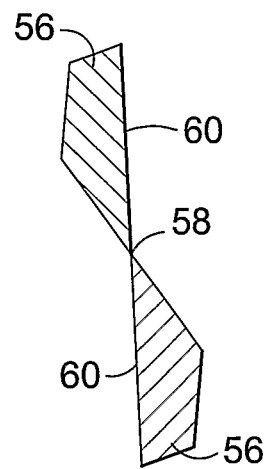
Figure 6:
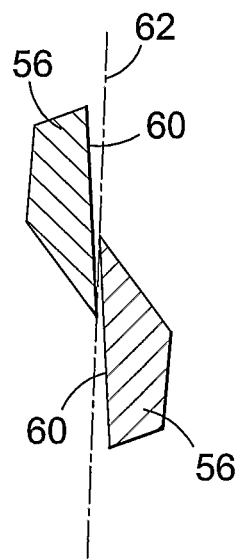
Figure 7:
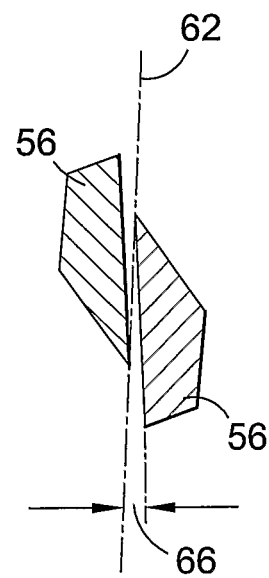

Referring now to FIG. 4, there is shown a cross-sectional diagrammatic representation of a cutting member 56 which may be used in the cutting assembly 18 shown in FIG. 3. The cutting member 56 includes a cutting edge 58 and an inner face 60 which is aligned from a cutting plane 62 at an angle 64, generally termed a relief angle. This relief angle 64 may be applied to each cutting member of the cutting assembly 18, as shown in FIG. 5, which ensures that once the cutting edges 58 of the cutting members 56 have made a cut, the inner faces 60 do not engage and establish a slight clearance 66 for the remainder of the cutting action, as shown in FIGS. 6 and 7. This arrangement provides a more efficient cutting action and substantially reduces any binding of the material between the blades 56.

Figure 8:
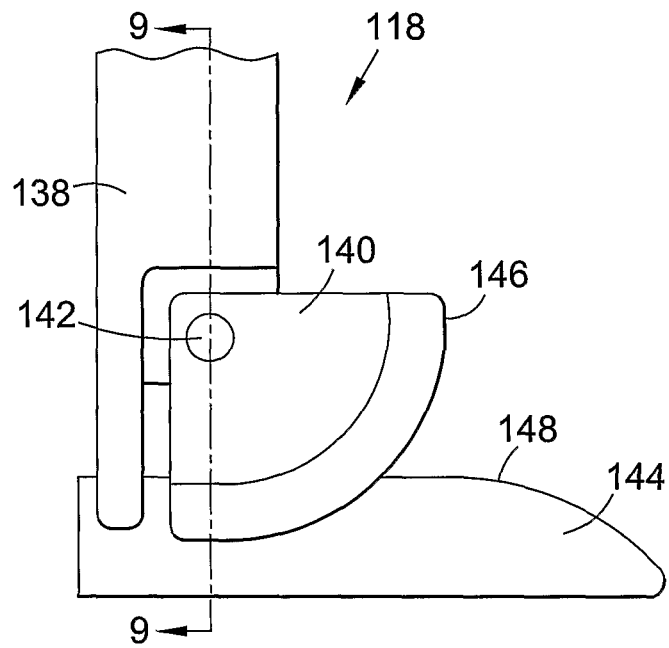

Reference is now made to FIG. 8 in which there is shown a diagrammatic side view of a cutting assembly, generally represented by reference numeral 118, of a cast-cutter in accordance with an embodiment of the present invention. The cutting assembly 118 is similar to the cutting assembly 18 shown in FIG. 3 and as such like components share like reference numerals, preceded by a '1'. The cutting assembly 118 includes a fixed cutting member 144 mounted on a support member 138. The fixed cutting member defines a single cutting edge 148. The cutting assembly 118 also includes a pivoting cutting member 140 pivotally mounted on a pivot 142 secured to the support member 138, wherein, in use, the pivot 142 is located above any material being cut. The pivoting member 140 defines a single cutting edge 146 such that when the pivoting member 140 is pivoted on the support member 138, cooperation of the cutting edges 146, 148 will cause any cast material located therebetween to be cut by a shearing action. In use, the arrangement shown in FIG. 8 will cause a single line of cut to be made in a cast material.

Figure 9:
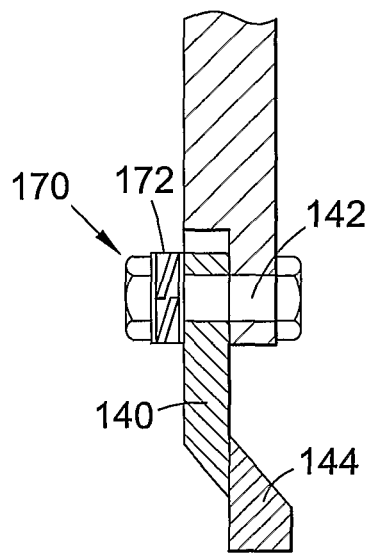

Reference is now additionally made to FIG. 9 which is a cross-sectional view of the cutting assembly 118 of FIG. 8, taken through line 9-9. As shown, the pivot 142 is provided by a nut and bolt arrangement 170 (this arrangement is not shown in FIG. 8 for clarity). Also shown is a sprung washer 172 compressed between part of the nut and bolt arrangement 170 and the pivoting member 140 of the cutting assembly 118. The sprung washer 172 acts to bias the pivoting member 140 against the fixed cutting member 144 to assist in preventing lateral separation of the members 140, 144 and to ensure an efficient cutting action is achieved and maintained.

Figure 10:
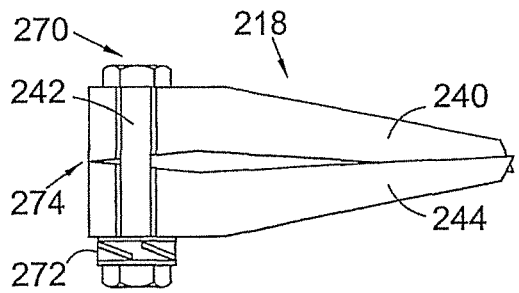
Figure 11:
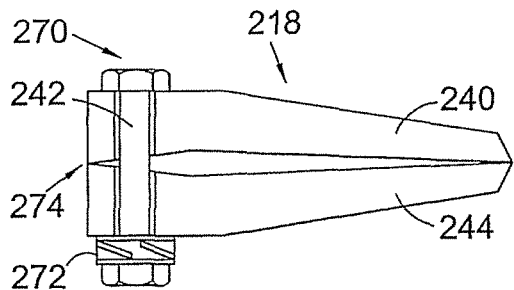

Reference is now made to FIGS. 10 and 11 which show a cutting assembly 218 for use in a cast-cutter in accordance with an embodiment of the present invention. The cutting assembly 218 includes first and second cutting members 240, 244 arranged to pivot relative to each other at pivot 242, provided by a nut and bolt arrangement 270. A spring 272 is provided in combination with the nut and bolt arrangement 270 to act to provide a pressing force between the members 240, 244 to assist in preventing splaying or separation of the members when in use. The members 240, 244 are shown in an open or "non-cut" position in FIG. 10, and in a closed or "cut" position in FIG. 11. Each member 240, 244 is formed with a longitudinal profile to cause an interference engagement between the members when moved from an open position to a closed position. This interference causes the spring 272 to become compressed, as shown in FIG. 11, which results in a greater spring force being applied between the members, to further assist in preventing separation of the members 240, 244 during cutting. The longitudinal profile may also be provided on the opposite side of the pivot point 242, in region 274.

Figure 12:
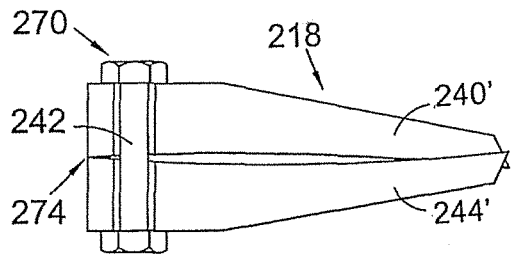
Figure 13:
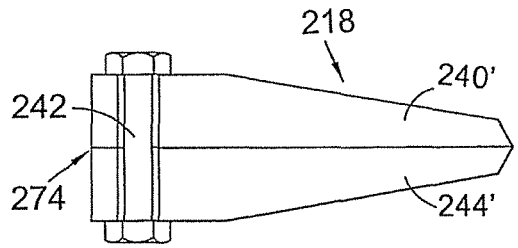

An alternative embodiment to that shown in FIGS. 10 and 11 is shown in FIGS. 12 and 13, wherein like components share like reference numerals. In this embodiment, the members 240', 244' of the cutting assembly 218' are longitudinally curved (FIG. 12), such that when the members are moved towards a closed position the members become straightened, as shown in FIG. 13, resulting in a force being applied between the members, with the force being contained by the nut and bolt arrangement 270. This force assists to prevent the members 240', 244' from becoming separated during a cutting operation. This arrangement therefore eliminates the requirement for the spring 272 shown in FIGS. 10 and 11. The members 240', 244' may also be curved on the opposite side of the pivot point 242, identified as region 274, to provide this same effect.

Figure 14:
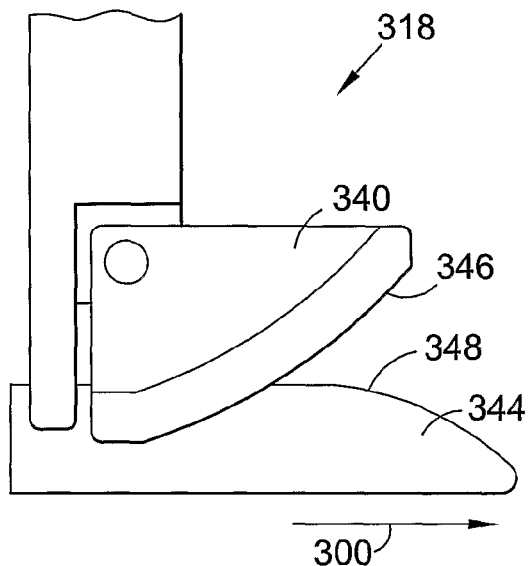
Figure 15:
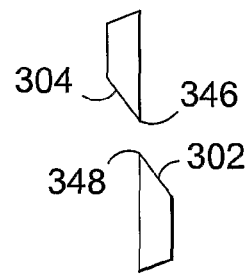

A general representation of a cutting assembly 318 is shown in FIGS. 14 and 15, in accordance with an embodiment of the present invention. As shown, a fixed cutting member 344 includes a generally horizontal cutting edge 348, wherein a pivoting cutting member 340 includes a curved cutting edge 346. Selection of a suitable curvature of this cutting edge 346 is important; a large radius of curvature requires an increased level of force to be applied to effect a cut, whereas a smaller radius of curvature may result in a material being forced outwards in the direction of arrow 300. Thus, an optimum radius of curvature should be selected which provides an efficient cutting action. Furthermore, careful selection of the slope 302, 304 of the respective cutting edges 348, 346 should be made in order to achieve the optimum sharpness; if the slope 302, 304 is too shallow then cutting may not be achieved, whereas if the slope 302, 304 is too steep then this may result in excessive wear on the cutting edges 346, 348, and may cause the edges to bind with each other.

Figure 16:
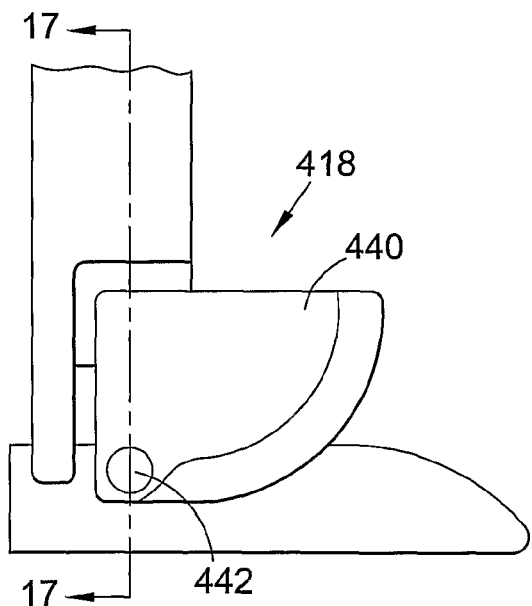
Figure 17:
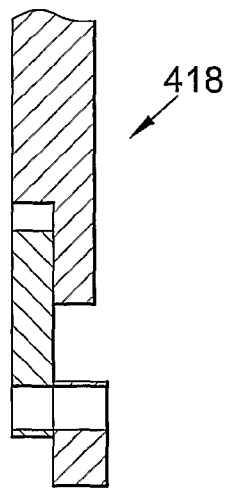

An alternative embodiment of a cutting assembly is shown in FIG. 16, designated by reference numeral 418, which is similar to that shown in FIG. 8 with the exception that a pivoting cutting member 440 of the cutting assembly 418 is mounted on a pivot 442 which is positioned below the line of cut. A cross-sectional view through line 17-17 of FIG. 16 is shown in FIG. 17. Although not shown, the cutting assembly 418 may include a nut and bolt arrangement and a spring as shown in FIG. 9.

A further alternative embodiment of a cutting assembly 518 is shown in FIGS. 18 and 19. FIG. 18 is a partial cross-sectional view through line 18-18 of FIG. 19, and FIG. 19 is a cross-sectional view through line 19-19 of FIG. 18. In this embodiment, a pivoting cutting member 540 defines an arcuate slot 576 through which a support 577 extends to support a fixed cutting member 544. Cutting member 540 is pivotally mounted on a support member 538 using a nut and bolt arrangement 570, which is provided in combination with a spring 572.

Referring now to FIG. 20, an alternative cutting assembly 618 is shown which includes a fixed cutting member 644 having first and second linearly aligned cutting edges 648a, 648b, and a generally semi-circular cutting member 640 pivotally mounted on a support member 638 via pivot 642. Cutting member 640 defines first and second cutting edges 646a, 646b adapted to cooperate with respective cutting edges 648a, 648b of the fixed member 644. Additionally, cutting member 640 defines an arcuate slot 676 through which a support 677 extends to engage and support cutting member 644. The support 677 is secured to the support member 638, such that the arrangement is similar to that shown in FIGS. 18 and 19. The embodiment shown in FIG. 20 is specifically adapted to cut a cast material in two opposite directions, providing a more versatile cast-cutter.

Figure 21:
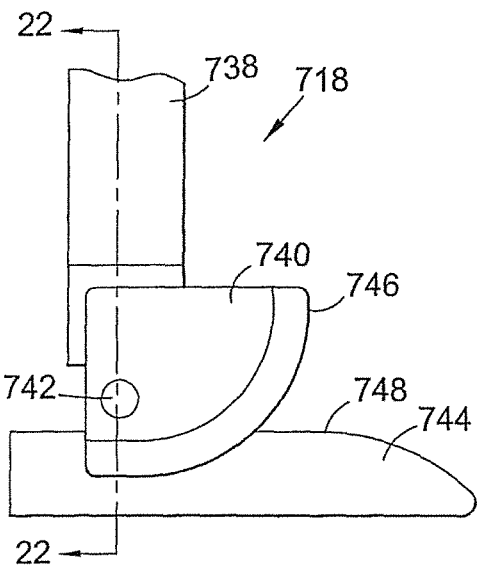
Figure 22:
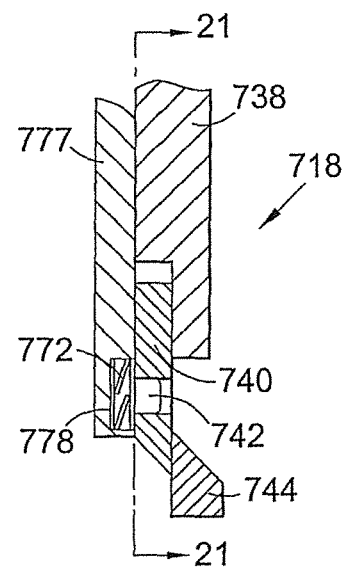

A further alternative cutting assembly 718 is shown in FIGS. 21 and 22; FIG. 21 is a cross-sectional view through line 21-21 of FIG. 22, and FIG. 22 is a cross-sectional view through line 22-22 of FIG. 21. The cutting assembly 718 includes a fixed cutting member 744 having a cutting edge 748, and a pivoting cutting member 740 also having a cutting edge 746 for cooperating with the cutting edge 748 of the fixed member 744. The pivoting member 740 is pivotally mounted on a support member 738 by way of a cantilever pivot pin 742 extending from a blind bore 778 in a support 777. A spring 772 is mounted within the blind bore 778 and acts to bias the cutting edges 746, 748 together.

Figure 23:
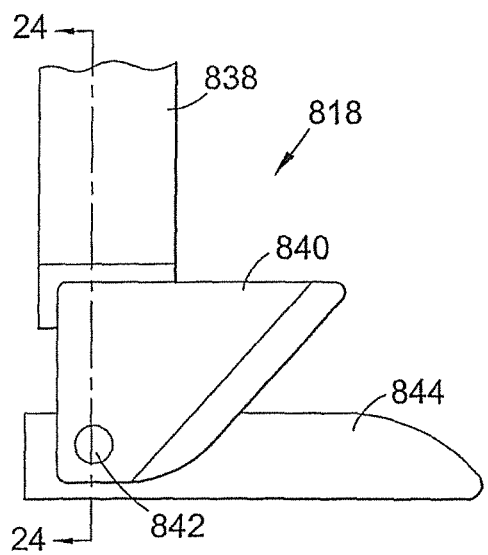
Figure 24:
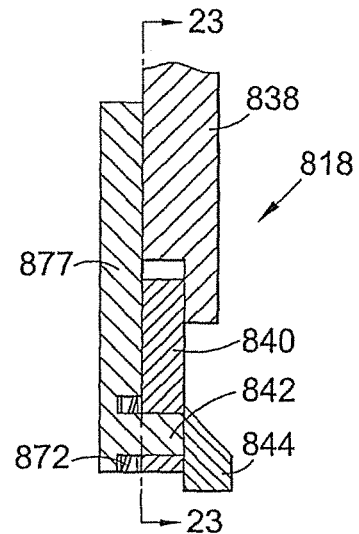

Another embodiment of a cutting assembly 818 for use in a cast-cutter according to the present invention is shown in FIGS. 23 and 24; FIG. 23 is a cross-sectional view through line 23-23 of FIG. 24, and FIG. 24 is a cross-sectional view through line 24-24 of FIG. 23. In this embodiment the cutting assembly 818 includes a pivoting cutting member 840 pivotally mounted on a fixed cutting member 844 by way of a pivot shaft 842 extending from a support 877, which support 877 is secured to a support member 838. A spring 872 is mounted around the pivot shaft, wherein the spring 872 acts to bias the cutting members 840, 844 into engagement.

Figure 25:
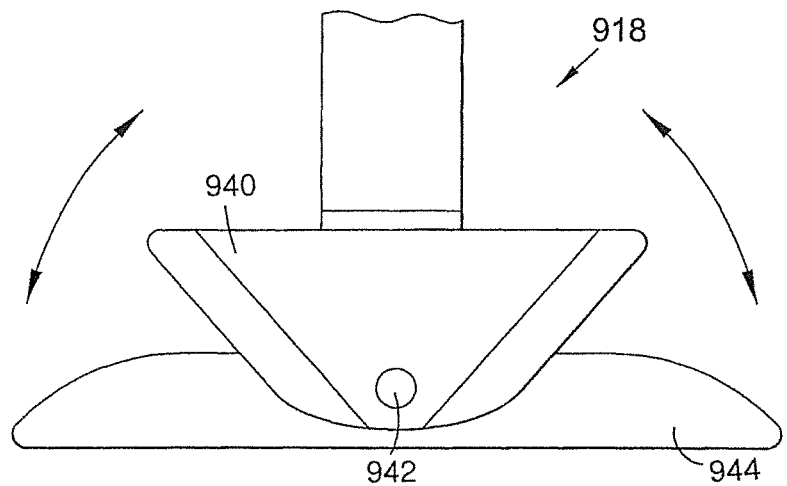

Reference is now made to FIG. 25 which is a diagrammatic representation of a cutting assembly 918 for a cast-cutter in accordance with an alternative embodiment of the present invention. This embodiment is similar to that shown in FIG. 20 with the exception that a pivoting cutting member 940 is pivotally mounted on a fixed cutting member 944 via pivot 942. As in the embodiment of FIG. 20, cutting assembly 918 allows cutting in two opposing directions.

Figure 26:
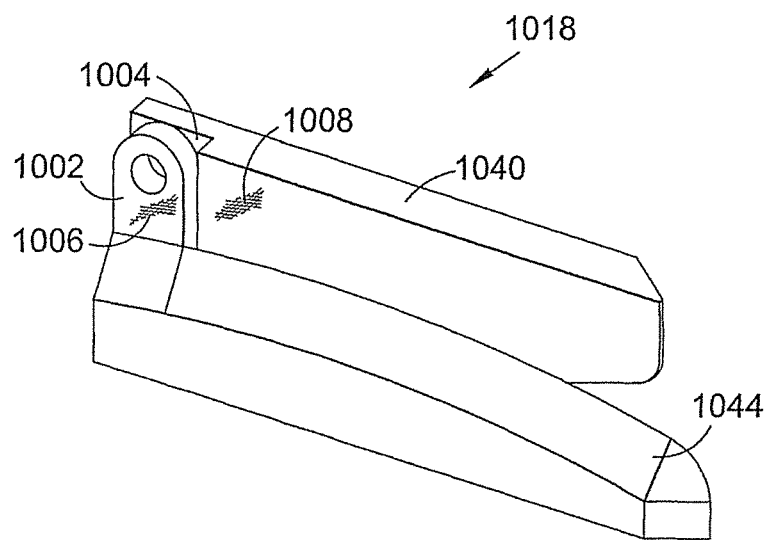

A further alternative cutting assembly 1018 is shown in FIG. 26. In this embodiment, a fixed cutting member 1044 includes a lug 1002, upon which lug 1002 a pivoting cutting member 1040 is pivotally mounted. The pivoting cutting member 1040 includes a land region or recess 1004 which accommodates the lug 1002. The recess 1004 is arranged such that when the cutting members 1040, 1044 are secured together, the surface 1006 of the lug is substantially flush with the surface 1008 of the pivoting member 1040 in order to present a low profile to any material being cut to minimise snagging of the material on the cutting assembly 1018.

Figure 27:
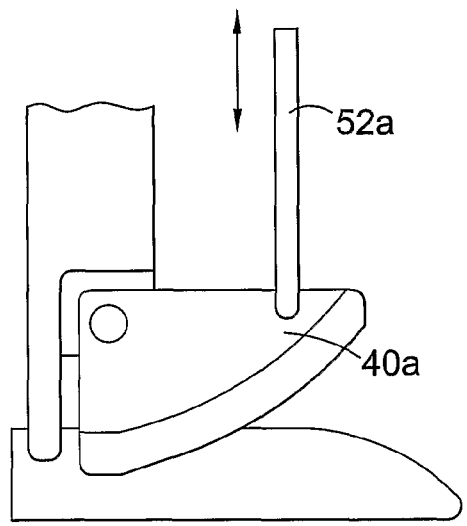
Figure 28:
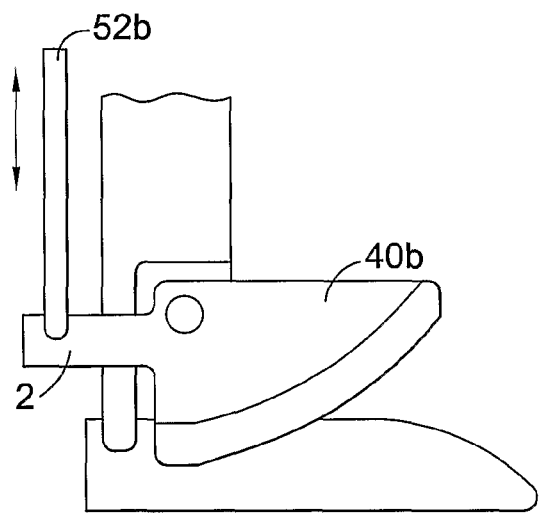

A drive mechanism for a cutting assembly having a pivoting cutting action is shown in FIG. 27, which is similar to that shown in FIG. 3. That is, a pivotally mounted cutting blade 40a is coupled to reciprocating drive means by a link 52a attached to a front portion of the blade 40a. An alternative embodiment is shown in FIG. 28 wherein a link 52b is attached to an extension portion 2 extending from the rear of the blade 40b. Where appropriate, the reciprocating drive means may be coupled directly to the blade 40a, 40b, without requiring a link 52a, 52b.

Figure 29:
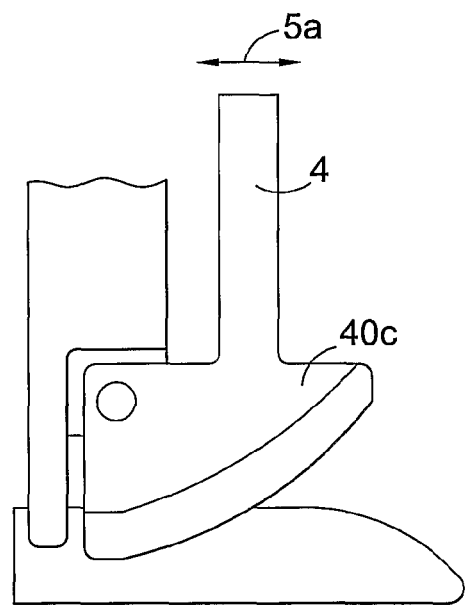
Figure 30:
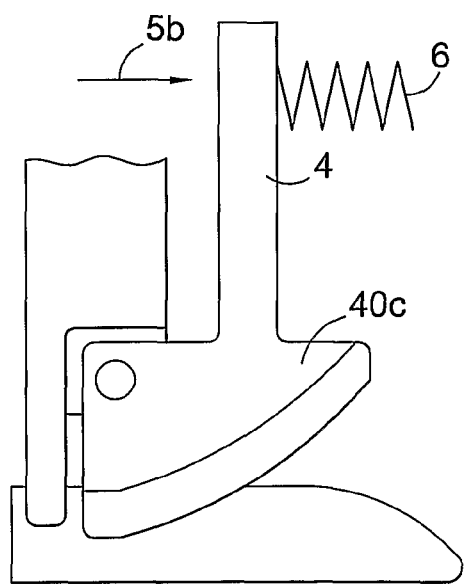

Alternative drive mechanisms are shown in FIGS. 29 and 30, wherein a pivoting blade 40c includes an extension portion 4 extending from an upper surface of the blade 40c, wherein a reciprocating drive mechanism such as a drive shaft and swash plate engages the extension portion 4 to cause motion in the direction of respective arrows 5a, 5b. The embodiment shown in FIG. 30 differs from that shown in FIG. 29 in that a spring 6 is provided which applies a return force on the extension portion 4 to cause or assist in the return of the extension portion 4 and blade 40c in the opposite direction to that designated by arrow 5b.

A further alternative drive mechanism is shown in FIG. 31, wherein a pivotally mounted cutting blade 40d includes an upper extension portion 1 defining a recess 7 which in use receives a rib 53 of a reciprocating drive member 52d. Thus, the reciprocating drive member 52d will cause the required pivoting motion of the blade 40d, which in cooperation with a fixed cutting blade 44d may be used to cut through a cast material. Upon connection of the entire cutting assembly or of at least the pivotally mounted blade 40d, there may be a misalignment of the recess 7 with the rib 53, as shown in FIG. 32. Thus, in one embodiment, the drive member 52d is arranged to be translated in the direction of arrow 8 (FIG. 32), thus allowing the drive member 52d to "pick-up" the blade 40d by engagement of the rib 53 with the recess 7. This particular arrangement may be utilised in various forms of drive mechanism, such as those shown in FIGS. 27 to 30. In an alternative embodiment (not shown), the drive member 52d may be arranged to be "parked" in a set location, which would accommodate for replacing the blade 40d or entire cutting assembly.

Figure 34A:
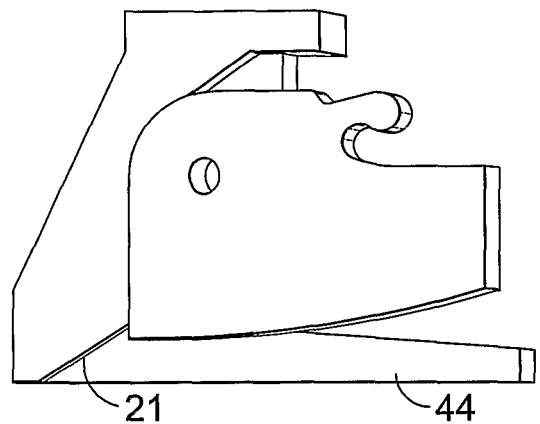
FIGS. 34a and 34b are reverse side perspective views of a cutting assembly in accordance with the present invention.
Figure 34B:
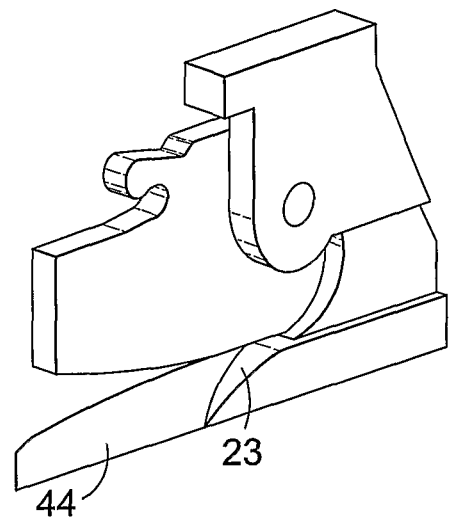

When a cast material is cut it has a natural tendency to splay slightly at the point of cut, as shown in FIG. 33 which is a diagrammatic perspective view of a cast material 11 having a cut section 13, wherein the cut section has a splayed separation generally represented by numeral 15. In one embodiment of the present invention, shown in FIG. 34, a fixed cutting member, such as member 44 of FIG. 3, is supported on the support member 38 through the natural splay 15 of a cast material being cut. In the embodiment shown, the support member 38 is generally wedge shaped. This wedge shape may additionally assist in separation of the cut edges 17, 19 of the material. Furthermore, as shown in FIGS. 34a and 34b, which show reverse side views of the cutting assembly 18 of FIG. 3, the fixed cutting member 44 incorporates relief or guide portions 21, 23, each relief or guide portion having a guide surface to engage a cast material being cut in order to assist in controlling the splay of the material in a preferred manner.

Figure 35:
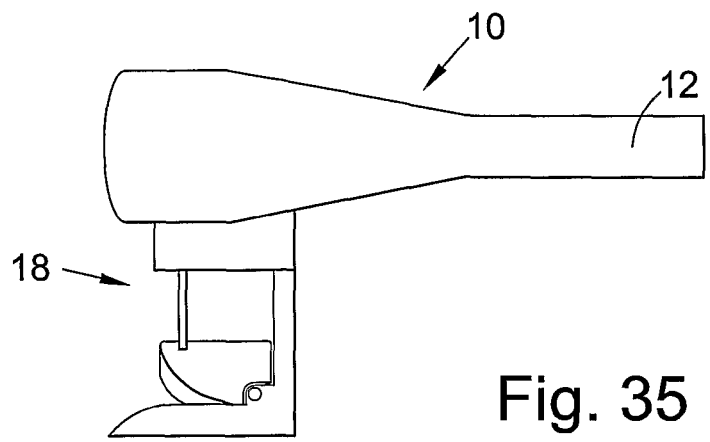
FIGS. 35 to 39 show various embodiments of a cast-cutter according to the present invention.
Figure 36:
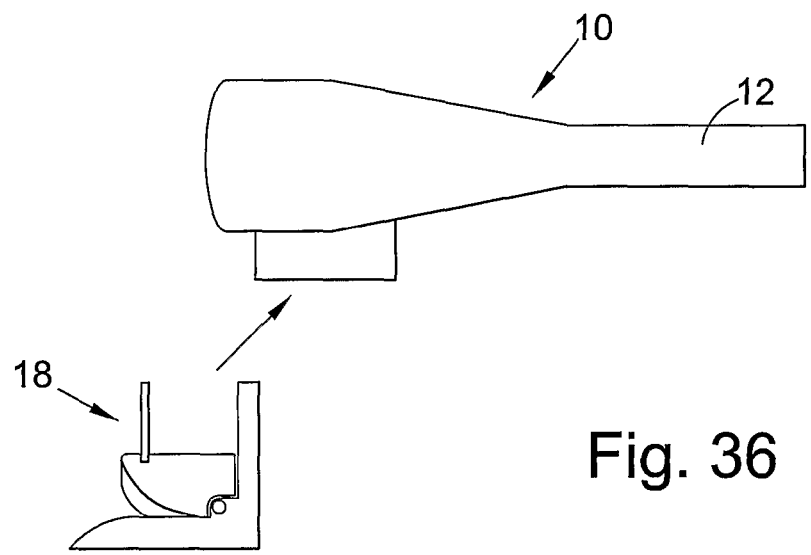
Figure 37:
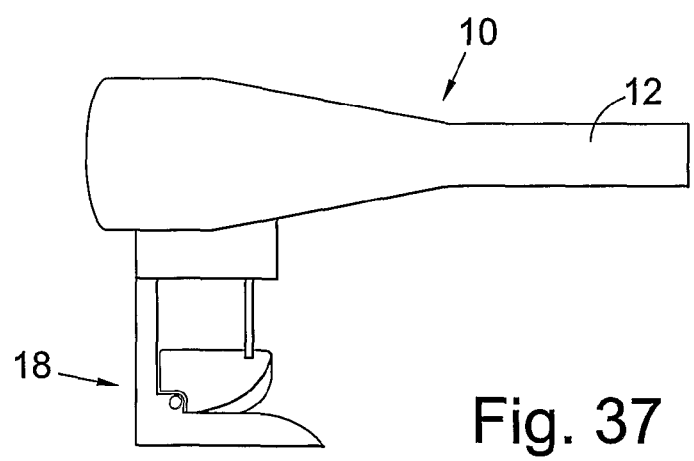

Reference is now made to FIGS. 35, 36 and 37 in which there is shown a simplified representation of the cast-cutter 10 of FIGS. 1 to 3. As shown in FIG. 36, the cutting assembly 18 may be removed from the body 12, and subsequently reattached to the body 12 in a reverse direction, as shown in FIG. 37. This particular arrangement allows the cast-cutter 10 to be operated in at least two directions of cut. Additionally, providing a cutting assembly 18 which is removable from the body 12 allows a used assembly to be removed and replaced with a new, sterile assembly, thus minimising the risk of transmitting infection between patients.

The arrangement may be such that different types of cutting assembly be reattached in accordance with the type or size of cast to be removed. Furthermore, it may be possible to change a particular cutting assembly for one which, for example, preferentially cuts a curve in a particular direction.

Figure 38:
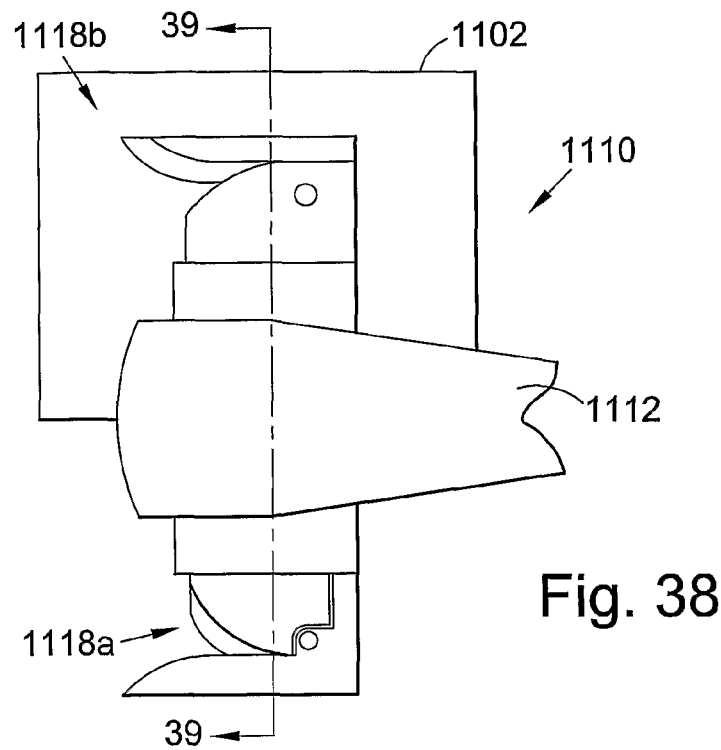
Figure 39:
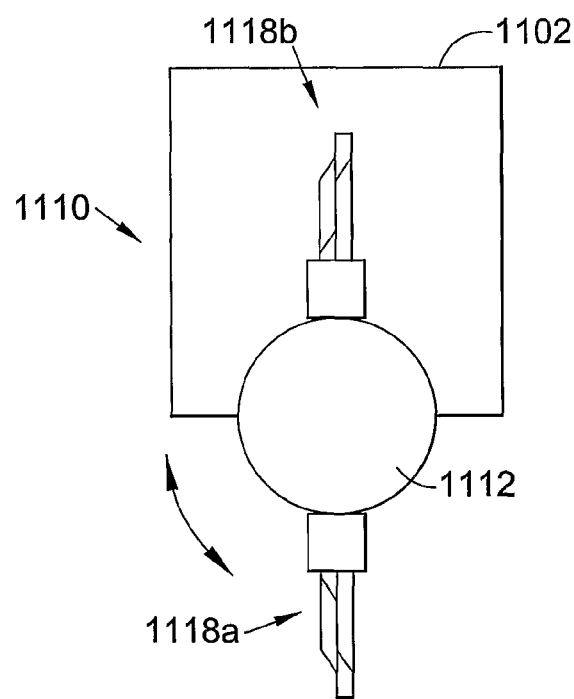

An alternative embodiment of a cast-cutter 1110 is shown in FIGS. 38 and 39, wherein FIG. 39 is a cross-sectional view of the cast-cutter of FIG. 38, taken along line 39-39. The cast-cutter includes a body 1112 upon which is mounted two diametrically opposed cutting assemblies 1118a, 1118b. The cast-cutter 1110 further includes a safety guard 1102 which may be fitted over the appropriate cutting assembly which is not in use, which in the embodiment shown is assembly 1118b.

Various embodiments of "linear action" cutting means for use with a cast-cutter in accordance with the present invention will now be described with reference to FIGS. 40 to 45.

Figures 40, 41:
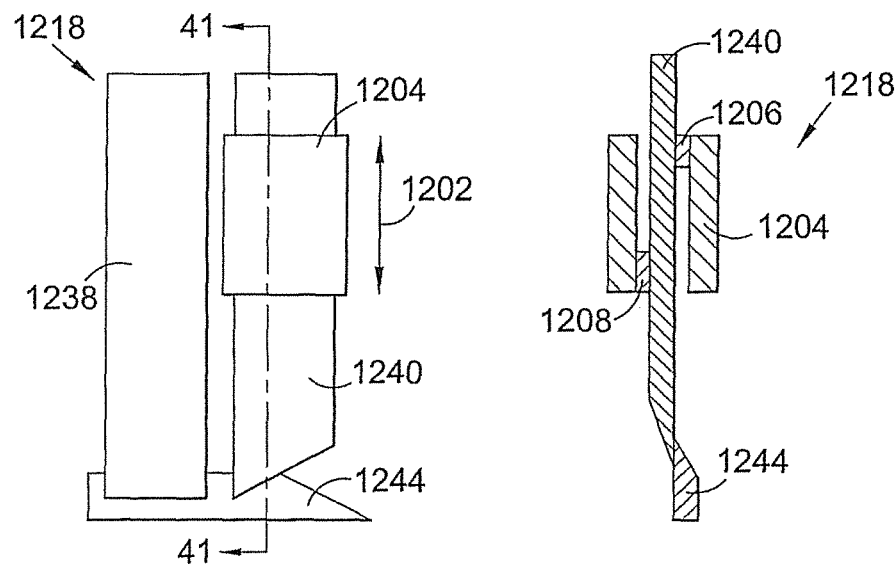
FIGS. 40 to 45 show various embodiments of cutting means which operate in a linear reciprocating motion in accordance with the present invention.

Reference is first made to FIGS. 40 and 41; FIG. 40 is a side view of a cutting assembly 1218 of a cast-cutter, and FIG. 41 is a cross-sectional view of the cutting assembly 1218 taken through line 41-41 of FIG. 40. The cutting assembly includes a fixed cutting member 1244 mounted on a support member 1238 (not shown in FIG. 41 for clarity) and a moveable cutting member 1240 mounted for reciprocating motion in the direction of arrow 1202. The moveable cutting member 1240 is slidably mounted within a sleeve 1204 which includes diagonally opposed locator ribs 1206, 1208 which act together to ensure a positive pressure between the cutting members 1240, 1244 to ensure an optimum cutting operation. Although not shown, this arrangement may additionally include biasing means to further assist in achieving a positive pressure between the cutting members 1240, 1244.

Figure 42:
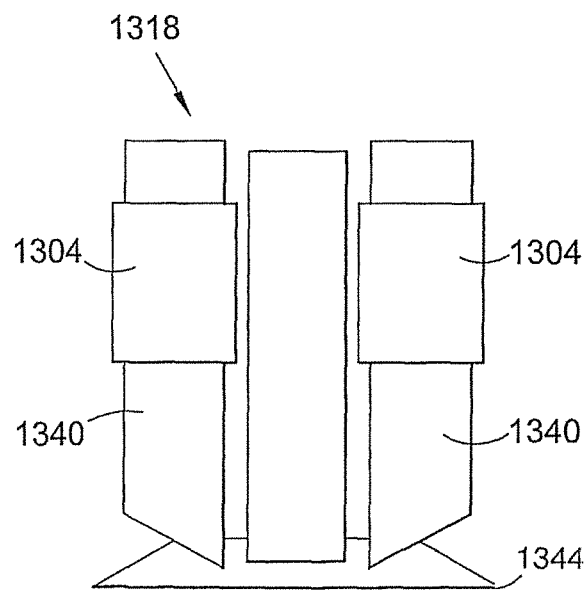

A variation of the embodiment shown in FIGS. 40 and 41 is shown in FIG. 42, wherein a dual action cutting assembly 1318 is provided which includes back-to-back cutting members 1340 and sleeves 1304 wherein the cutting members 1340 cooperate with fixed cutting member 1344 to allow the cast-cutter to be readily operated in reverse directions.

Figure 43:
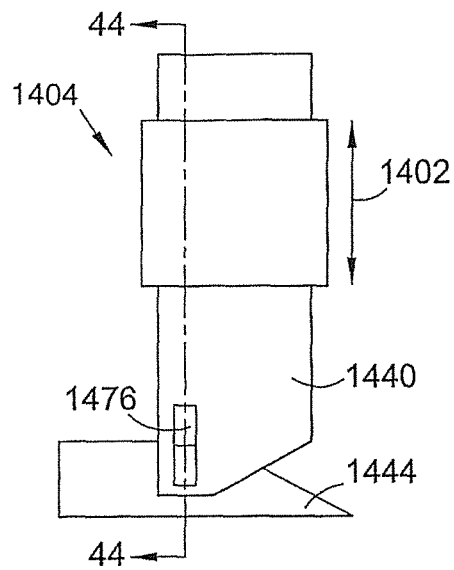
Figure 44:
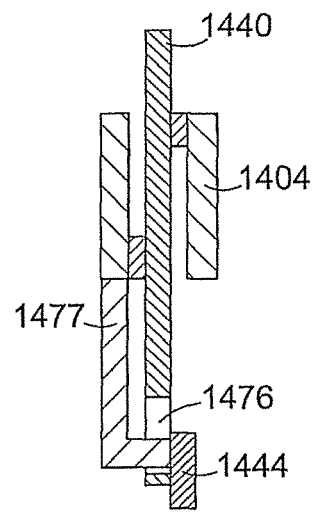

A further alternative embodiment of a cutting assembly 1418 is shown in FIGS. 43 and 44, wherein FIG. 44 is a cross-sectional view through line 44-44 of FIG. 43. In this embodiment a fixed cutting member 1444 is provided which is attached to a support 1477 (FIG. 44), which support 1477 is attached to a sleeve 1404. The support 1477 is not shown in FIG. 43 for clarity. A moveable cutting member 1440 is provided which is arranged to reciprocate in the direction of arrow 1402, wherein the moveable cutting member 1440 defines a slot 1476 adapted to accommodate the support 1477. The moveable cutting member 1440 is slidably mounted within the sleeve 1404, which is similar to sleeve 1204 of FIGS. 40 and 41, and as such no further description will be given.

Figure 45:
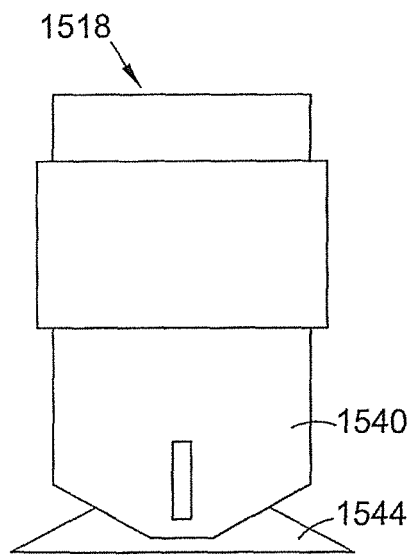

Reference is now made to FIG. 45 which shows a cutting assembly 1518 similar to that shown in FIGS. 43 and 44, with the exception that the fixed and moveable cutting members 1544, 1540 are adapted to be used to cut in opposing directions.

A number of alternative embodiments have been described above in accordance with aspects of the present invention. It should be appreciated that these various embodiments may be used in various combinations and are not limited for use as specifically shown and described.

Figure 46:
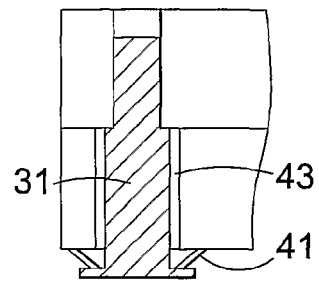
FIGS. 46 to 48 are diagrammatic representations of pivot connections for pivotally mounting a pivoting cutting member in accordance with embodiments of the present invention.
Figure 47:
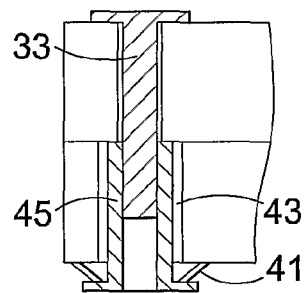
Figure 48:
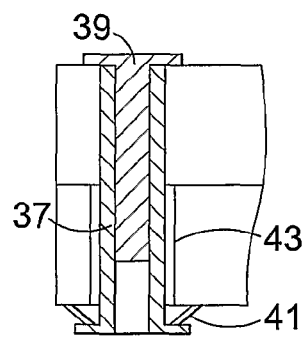

It should be understood that the various embodiments described are merely exemplary of the present invention and that various modifications may be made thereto without departing from the scope of the invention. For example, in FIGS. 9 to 13 a pivot connection is provided by a nut and bolt arrangement to pivotally support the pivoting cutting member. However, other suitable pivot connections may be utilised, such as shown in FIGS. 46 to 48. That is, in the connection shown in FIG. 46, a pivot pin 31 is secured to one of the cutting members of the cutting assembly. The pin may be secured by, for example, a press fit or a threaded connection or the like. In the connection shown in FIG. 47, a pivot pin is provided in two sections 33, 45 which may be press fitted together or alternatively may be secured together by a threaded connection. An arrangement similar to that shown in FIG. 47 is shown in FIG. 48, wherein a pivot pin is provided in two portions 37, 39 with one portion extending along the entire width of both the cutting members.

Also shown in FIGS. 46 to 48 is a disc spring 41 which may be used in place of the sprung washer shown for example in FIG. 9.

Further, in each of the arrangements shown in FIGS. 46 to 48 an annulus 43 is provided to establish a clearance between the pin and one of the cutting members to permit a degree of rocking of one of the cutting members to thus accommodate movement due to the cross over displacement as the blades operate.

The invention claimed is:

1. A cast-cutter for use in removing a cast from a patient, said cast-cutter comprising:
   a body;
   a motor disposed in the body;
   a cutting assembly mounted on the body and driven by the motor, the cutting assembly comprising first and second cutting members each defining a cutting edge and an inner face, the first and second cutting members being pivotable relative to each other about a pivot axis, the relative movement of the cutting edges defining a cutting plane, the respective cutting edges cooperating with one another in the cutting plane to cut cast material by a shearing action along a line of cut within the cutting plane while maintaining the inner faces in non-engaging relationship to provide clearance therebetween;
   wherein the pivot axis is offset from the line of cut;
   wherein the first cutting member includes first and second guide portions arranged on opposing sides of the cutting edge of the first cutting member, the first and second guide portions further being arranged on opposing sides of the cutting plane; and
   wherein the first and second guide portions each includes a guide surface, the guide surfaces facing in substantially opposite directions and one of the guide surfaces facing in generally the same direction that the cutting edge of the first cutting member faces, whereby the guide surfaces are positioned to engage cut portions of the cast material to assist in controlling the splay of the cast material as it is being cut.

2. A cast-cutter according to claim 1, wherein the inner face of at least one of the cutting members is inclined outwardly from the cutting plane in order to provide said clearance between the inner faces when the cutting assembly is operated.

3. A cast-cutter as claimed in claim 1, wherein the inner face of each cutting member is outwardly inclined from the cutting plane in order to provide said clearance between said faces when the cutting assembly is operated.

4. A cast-cutter according to claim 1, wherein the pivot axis is located substantially above the line of cut.

5. A cast-cutter according to claim 1, wherein the pivot axis is located substantially below the line of cut.

6. A cast-cutter according to claim 1, wherein the location of the pivot axis permits the transport of material under the pivot axis, without the pivot axis passing through the material.

7. A cast-cutter according to claim 1, further comprising a support member wherein the first cutting member is rigidly mounted on the support member and the second cutting member is pivotally mounted on the support member.

8. A cast-cutter according to claim 1, wherein the guide surface of the first guide portion assists in splaying the cast material downwards, and the guide surface of the second guide portion assists in splaying the cast material upwards.

9. A cast-cutter according to claim 1, wherein the cutting plane is a vertical cutting plane, and the guide portions assist in controlling a horizontal splay of the cast.

10. A cast-cutter according to claim 1, wherein the guide portions comprise ramped guide portions.

11. A method of removing a cast from a patient, said method comprising the steps of:
    providing a cast cutter including:
       a body,
       a motor disposed in the body, and
       a cutting assembly mounted on the body and driven by the motor, the cutting assembly comprising first and second cutting members each defining a cutting edge and an inner face, the first and second cutting members being pivotable relative to each other about a pivot axis, the relative movement of the cutting edges defining a cutting plane, the respective cutting edges cooperating with one another in the cutting plane to cut by a shearing action along a line of cut within the cutting plane while maintaining the inner faces in non-engaging relationship to provide clearance therebetween,
       wherein the pivot axis is offset from the line of cut, and first and second guide portions forming part of the first cutting member and arranged on opposing sides of the cutting edge of the first cutting member, the first and second guide portions further being arranged on opposing sides of the cutting plane;
    manipulating the cast-cutter to position a cast material to be removed from a patient between the first and second cutting members; and
    activating the cast-cutter to cause the relative movement of the first and second cutting members to cause the cast material to be cut by the cooperation of the cutting edges, with the first guide portion having a guide surface that is downwardly facing relative to the cutting edge of the first cutting member and the second guide portion having a guide surface that is upwardly facing relative to the cutting edge of the first cutting member, the guide surfaces engaging cut portions of the cast material to assist in controlling the splay of the cast material as it is being cut.

* * * * *